US005696147A

United States Patent [19]

Galardy

[11] Patent Number: 5,696,147
[45] Date of Patent: Dec. 9, 1997

[54] INHIBITION OF ANGIOGENESIS BY SYNTHETIC MATRIX METALLOPROTEASE INHIBITORS

[75] Inventor: Richard E. Galardy, Suilford, Conn.

[73] Assignee: Glycomed, Inc., Alameda, Calif.

[21] Appl. No.: 161,786

[22] Filed: Dec. 3, 1993

Related U.S. Application Data

[63] Continuation of Ser. No. 817,039, Jan. 7, 1992, Pat. No. 5,268,384, which is a continuation-in-part of Ser. No. 747,751, Aug. 20, 1991, Pat. No. 5,239,078, Ser. No. 747,752, Aug. 20, 1991, Pat. No. 5,189,178, and Ser. No. 615,798, Nov. 21, 1990, Pat. No. 5,183,900.

[51] Int. Cl.$^6$ ........................ A61K 31/405; A61K 31/445
[52] U.S. Cl. ........................ 514/419; 514/323; 514/563; 514/620; 514/626
[58] Field of Search ........................ 514/323, 419, 514/563, 620, 626

[56] References Cited

U.S. PATENT DOCUMENTS

| 4,291,048 | 9/1981 | Gold | 546/201 |
|---|---|---|---|
| 4,558,034 | 12/1985 | Galardy et al. | 514/7 |
| 4,599,361 | 7/1986 | Dickens et al. | 514/575 |
| 4,681,894 | 7/1987 | Murray et al. | 548/495 |
| 4,698,342 | 10/1987 | Crosby | 514/575 |
| 4,743,587 | 5/1988 | Dickens et al. | 514/575 |
| 4,918,105 | 4/1990 | Cartwright et al. | 514/575 |
| 4,943,587 | 7/1990 | Cetenko et al. | 548/495 |
| 4,996,358 | 2/1991 | Handa et al. | 562/623 |
| 5,183,900 | 2/1993 | Galardy et al. | 546/201 |
| 5,189,178 | 2/1993 | Galardy et al. | 548/495 |
| 5,239,078 | 8/1993 | Galardy et al. | 546/201 |
| 5,304,604 | 4/1994 | Davidson et al. | 514/238.2 |
| 5,453,438 | 9/1995 | Campion et al. | 514/424 |

FOREIGN PATENT DOCUMENTS

| 0082088 | 6/1983 | European Pat. Off. |
|---|---|---|
| 0159396 | 10/1984 | European Pat. Off. |
| 0126974 | 12/1984 | European Pat. Off. |
| 0 236 872 B1 | 2/1987 | European Pat. Off. |
| 0276436 | 8/1988 | European Pat. Off. |
| 0 445 206 B1 | 11/1989 | European Pat. Off. |
| 0489579 | 6/1992 | European Pat. Off. |
| 57-058626 | 4/1982 | Japan. |
| WO 88/06890 | 9/1988 | WIPO. |
| WO 90/05716 | 5/1990 | WIPO. |
| WO 91/02716 | 3/1991 | WIPO. |

OTHER PUBLICATIONS

Dialog™ Computer Database Abstract of International (PCT) Patent No. WO 91/11193 (Jan. 25, 1991).
Dialog™ Computer Database Abstract of European Patent Application No. 0424193 (Apr. 24, 1991).
Mullins et al., "The role of proteinases in cellular invasiveness" *Biochem. Biophys. Acta* (1983) 695:177–214.
Reich et al., "Effects of inhibitors of plasminogen activator, serine proteinases, and collagenases IV on the invasion of basement membranes by metastatic cells" (1988) *Cancer Res.* (1988) 48:3307–3312.
Nishino et al., "Design of potent reversible inhibitors for thermolysin. Peptides containing zinc coordinating ligands and their use in affinity chromatography" *Biochemistry* (1979) 18:4340–4347.
Nishino et al., "Peptide hydroxamic acids an inhibitors of thermolysin" *Biochemistry* (1978) 17:2846–2850.
G. S. Schultz et al., "Treatment of Alkali–Injured Corneas With a Synthetic Inhibitor of Matrix Metalloprotease" *Investigative Ophthalmology & Visual Science*, vol. 33, No. 12, pp. 3325–3331, Nov. 1992.

*Primary Examiner*—Joseph McKane
*Attorney, Agent, or Firm*—Lyon & Lyon LLP

[57] ABSTRACT

Synthetic mammalian matrix metalloprotease inhibitors are useful in controlling angiogenesis. These compounds are thus useful in controlling the growth of tumors and in controlling neovascular glaucomas.

13 Claims, No Drawings

INHIBITION OF ANGIOGENESIS BY SYNTHETIC MATRIX METALLOPROTEASE INHIBITORS

This application is a continuation of application Ser. No. 07/817,039 filed Jan. 7, 1992, now U.S. Pat. No. 5,268,384, which is a continuation-in-part of U.S. Ser. No. 07/747,751, filed 20 Aug. 1991, now U.S. Pat. No. 5,239,078; and a CIP of 07/747,752, filed 20 Aug. 1991, now U.S. Pat. No. 5,189,178, and a CIP of 07/615,798, filed 21 Nov. 1990, now U.S. Pat. No. 5,183,900.

TECHNICAL FIELD

This invention is directed to pharmaceuticals which are useful in diseases characterized by unwanted collagenase activity. More specifically, the invention concerns hydroxamates which are dipeptide analogs that include fused or conjugated bicycloaryl substituents, substituted or unsubstituted hydroxamates which include fused or conjugated bicycloaryl substituents, and substituted or unsubstituted hydroxyureas and reverse hydroxamates and which include fused or conjugated bicycloaryl substituents.

RELEVANT ART

There are a number of enzymes which effect the breakdown of structural protein and which are structurally related metalloproteinases. These include human skin fibroblast collagenase, human skin fibroblast gelatinase, human sputum collagenase and gelatinase, and human stromelysin. These are zinc-containing metalloproteinase enzymes, as are the angiotensin-converting enzymes and enkephalinases.

Collagenase and related enzymes are important in mediating the symptomology of a number of diseases, including rheumatoid arthritis (Mullins, D. E., et al., *Biochim Biophys Acta* (1983) 695:117-214); the metastasis of tumor cells (ibid., Broadhurst, M. J. et al., EP application 276436 (1987), Reich, R., et al., *Cancer Res* (1988) 48:3307-3312); and various ulcerated conditions. Ulcerative conditions can result in the cornea as the result of alkali burns or as a result of infection by *Pseudomonas aeruginosa*, Acanthamoeba, *Herpes simples* and vaccinia viruses. Other conditions characterized by unwanted matrix metalloprotease activity include periodontal disease, epidermolysis bullosa and scleritis.

In view of the involvement of collagenase in a number of disease condition, attempts have been made to prepare inhibitors to this enzyme. A number of such inhibitors are disclosed in EP applications 126,974 (published 1984) and 159,396 (published 1985) assigned to G. D. Searle. These inhibitors are secondary amines which contain oxo substituents at the 2-position in both substituents bonded to the amino nitrogen.

More closely related to the compounds of the present invention are those disclosed in U.S. Pat. Nos. 4,559.361 and 4,743,587, also assigned to G. D. Searle. These compounds are hydroxylamine dipeptide derivatives which contain, as a part of the compound, a tyrosine or derivatized tyrosine residue or certain analogs thereof.

Other compounds that contain sulfhydryl moieties as well as residues of aromatic amino acids such as phenylalanine and tryptophan are disclosed in PCT application WO88/06890. Some of these compounds also contain i-butyl side chains.

Inhibitors have also been disclosed for the related protease, thermolysin. These include hydroxamic peptide derivatives described by Nishino, N., et al., *Biochemistry* (1979) 18:4340-4347; Nishino, N., et al., *Biochemistry* (1978) 17:2846-2850. Tryptophan is also known to be therapeutic in various conditions, some of which may involve collagenase (see, for example, JP 57/058626; U.S. Pat. Nos. 4,698,342; 4,291,048). Also, inhibitors of bacterial collagenases have been disclosed in U.S. Pat. No. 4,558,034.

It has now been found that the compounds described below have superior inhibiting activity with respect to matrix metalloproteases. The invention compounds add to the repertoire of agents available for the treatment of conditions and diseases which are characterized by unwanted activity by the class of proteins which destroy structural proteins and designated "matrix metalloprotease" herein.

Angiogenesis is defined as the growth of new blood vessels, in particular, capillaries. The ingrowth of such capillaries and ancillary blood vessels is essential for tumor growth and is thus an unwanted physiological response which encourages the spread of malignant tissue and metastases. Inhibition of angiogenesis is therefore envisioned as a component of effective treatment of malignancy. Neovascularization of the eye is a major cause of blindness. One form of this condition, proliferative diabetic retinopathy, results from diabetes; blindness can also be caused by neovascular glaucoma. Inhibition of angiogenesis is useful in treating these conditions also.

PCT application WO 91/11193, published 25 Jan. 1991 describes the isolation of a collagenase inhibitor from cartilage which inhibits the formation of blood vessels. This composition, designated cartilage-derived inhibitor (CDI), is reported to inhibit tumor-induced angiogenesis in the rabbit corneal pocket assay and to inhibit capillary tube formation. It is further speculated that other collagenase inhibitors such as peptides or antibodies immunoreactive with collagenase will also have the ability to inhibit blood vessel formation.

In addition, EP application 424,193 published 24 Apr. 1991, describes the activity of actinonin as an angiogenesis inhibitor. Actinonin is an antibiotic produced by a particular strain of Streptomyces and is a modified peptide structure.

As disclosed in the two foregoing applications, unwanted levels of angiogenesis are present not only in association with tumor growth, but also are the cause of blindness resulting from diabetic retinopathy and other ocular pathologies.

The present invention supplies alternative compounds that are useful in the inhibition of angiogenesis, and which can be supplied as synthetic compounds in isolated and purified form.

DISCLOSURE OF THE INVENTION

The invention provides new compounds which are useful as inhibitors of matrix metalloproteases and which are effective in treating conditions characterized by excess activity of these enzymes. In addition, these compounds can be used to purify matrix metalloproteases and to detect increased levels of matrix metalloproteases in vivo. The compounds take advantage of the incorporation of tryptophan or other fused or conjugated bicycloaromatic amino acid residues in a hydroxamate-derivatized dipeptide matrix metalloprotease inhibitor or into a substituted or unsubstituted reverse hydroxamate- or a hydroxyurea-derivatized matrix metalloprotease inhibitor or into a substituted or unsubstituted hydroxamate-derivatized matrix metalloprotease inhibitor.

The methods and compositions of the invention for control of angiogenesis comprise, as an active ingredient, at least one synthetic metalloprotease inhibitor. Some members of this class of compounds are known in the art; others are described and claimed in U.S. Ser. Nos. 07/747,751, filed 20 Aug. 1991; 07/747,752, filed 20 Aug. 1991; and 07/615,798, filed 21 Nov. 1990, the disclosures of which are incorporated herein by reference.

A summary of the art-known synthetic matrix metalloprotease inhibitors is found in EP application 423,943 published 24 Apr. 1991. This application assembles the structures of the synthetic matrix metalloproteases known in the art and claims their use in the treatment of demyelinating diseases of the nervous system. The present invention is directed to the use of these compounds, as well as those disclosed in the above-referenced U.S. applications, in inhibiting angiogenesis.

Thus, in one aspect, the invention is directed to a method to inhibit angiogenesis which method comprises administering, to the site at which unwanted angiogenesis occurs, an effective amount of at least one synthetic mammalian matrix metalloprotease inhibitor. In other aspects, the invention is directed to compositions useful in inhibiting angiogenesis containing, as an active ingredient, at least one synthetic mammalian matrix metalloprotease inhibitor.

MODES OF CARRYING OUT THE INVENTION

The angiogenesis inhibitory compounds of the invention are synthetic inhibitors of mammalian matrix metalloproteases. Matrix metalloproteases include without limitation human skin fibroblast collagenase, human skin fibroblast gelatinase, purulent human sputum collagenase and gelatinase, and human stromelysin. These are zinc-containing metalloprotease enzymes, as are the angiotensin-converting enzymes and the enkephalinases. As used herein, "mammalian matrix metalloprotease" means any zinc-containing enzyme found in mammalian sources that is capable of catalyzing the breakdown of collagen, gelatin or proteoglycan under suitable assay conditions.

Appropriate assay conditions can be found, for example, in U.S. Pat. No. 4,743,587, which references the procedure of Cawston, et al., *Anal Biochem* (1979) 99:340–345, use of a synthetic substrate is described by Weingarten, H., et al., *Biochem Biophys Res Comm* (1984) 139:1184–1187. Any standard method for analyzing the breakdown of these structural proteins can, of course, be used. The matrix metalloprotease enzymes referred to in the herein invention are all zinc-containing proteases which are similar in structure to, for example, human stromelysin or skin fibroblast collagenase.

The ability of candidate compounds to inhibit matrix metalloprotease activity can, of course, be tested in the assays described above. Isolated matrix metalloprotease enzymes can be used to confirm the inhibiting activity of the invention compounds, or crude extracts which contain the range of enzymes capable of tissue breakdown can be used.

Specifically, assays of inhibition activity can be conducted as follows. Inhibitors may be assayed against crude or purified human skin fibroblast collagenase using the synthetic thiol ester substrate at pH 6.5 exactly as described by Kortylewicz & Galardy, *J Med Chem* (1990) 33:263–273, at a collagenase concentration of 1–2 nM. The candidate inhibitors are tested for their ability to inhibit crude collagenase and gelatinase from human skin fibroblasts and from purulent human sputum in this assay. The results may be set forth in terms of Ki, i.e., the calculated dissociation constant for the inhibitor complex with enzyme. Ki values for effective inhibitors are $\leq 500$ nM for purified enzyme in this assay. For purified human skin collagenase, excellent inhibitors show Ki values of $\leq 10$ nM. Assays for inhibition of human stromelysin are conducted as described by Teahan, J., et al., *Biochemistry* (1989) 20:8497–8501.

The synthetic compounds that are successful in these assays for mammalian matrix metalloprotease inhibition are generally small molecules containing at least one amide bond and have a variety of sidechain substituents. Examples of such compounds known in the art are given, as set forth above, in EP application publication no. 423,943, incorporated herein by reference.

Other suitable inhibitors are of the formula:

or

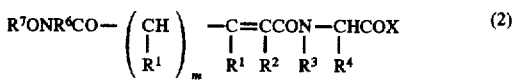

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated unsubstituted or substituted bicycloaryl methylene;

n is 0, 1 or 2;

m is 0 or 1; and

X is $OR^5$ or $NHR^5$, wherein $R^5$ is H or substituted or unsubstituted alkyl (1–12C), aryl (6–12C), aryl alkyl (6–16C); or X is an amino acid residue or amide thereof; or X is the residue of a cyclic amine or hetero-cyclic amine; and $R^6$ is H or lower alkyl (1–4C) and $R^7$ is H, lower alkyl (1–4C) or an acyl group, and wherein the —$CONR^3$— amide bond shown is optionally replaced by a modified isosteric bond, such as —$CH_2NR^3$—, —$CH_2CHR^3$—, —$CH=CR^3$—, —$COCHR^3$—, —$CHOHCHR^3$—, —$NR^3CO$—, —$CF=CR^3$—, and the like.

Other compounds useful in the method of the invention include compounds of the formulas

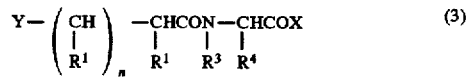

or

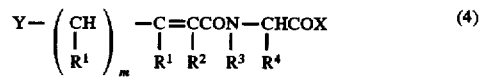

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated unsubstituted or substituted bicycloaryl methylene;

n is 0, 1 or 2;

m is 0 or 1; and

X is $OR^5$ or $NHR^5$, wherein $R^5$ is H or substituted or unsubstituted alkyl (1–12C), aryl (6–12C), aryl alkyl (6–16C); or X is an amino acid residue or amide thereof; or X is the residue of a cyclic amine or hetero-cyclic amine;

Y is selected from the group consisting of $R^7ONR^6CONR^6-$, $R^6{}_2NCONR^7-$, and $R^6CONR^7-$, wherein each $R^6$ is independently H or lower alkyl (1–4C); $R^7$ is H, lower alkyl (1–4C) or an acyl group, and wherein the $-CONR^3-$ amide bond shown is optionally replaced by a modified isosteric bond, such as $-CH_2NR^3-$, $-CH_2CHR^3-$, $-CH=CR^3-$, $-COCHR^3-$, $-CHOHCHR^3-$, $-NR^3CO-$, $-CF=CR^3-$, and the like.

"Alkyl" has its conventional meaning as a straight chain, branched chain or cyclic saturated hydrocarbyl residue such as methyl, ethyl, isobutyl, cyclohexyl, t-butyl or the like. The alkyl substituents of the invention are of the number of carbons noted which may be substituted with 1 or 2 substituents. Substituents are generally those which do not interfere with the activity of the compound, including hydroxyl, "CBZ," amino, and the like. Aryl refers to aromatic ring systems such as phenyl, naphthyl, pyridyl, quinolyl, indolyl, and the like; aryl alkyl refers to aryl residues linked to the position indicated through an alkyl residue. In all cases the aryl portion may be substituted or unsubstituted. "Acyl" refers to a substituent of the formula RCO— wherein R is alkyl or arylalkyl as above-defined. The number of carbons in the acyl group is generally 1–15; however as the acyl substitute is readily hydroxylized in vivo the nature of the group is relatively unimportant. "Cyclic amines" refer to those amines where the nitrogen is part of a heterocyclic ring, such as piperidine, "heterocyclic amines" refer to such heterocycles which contain an additional heteroatom, such as morpholine.

In the compounds of formulas 1 and 3, preferred embodiments for $R^1$ and $R^2$ include those wherein each $R^1$ is H or Me and $R^2$ is alkyl of 3–8C, especially isobutyl, 2-methyl butyl, or isopropyl. Especially preferred is isobutyl. Preferred also are those compounds of all of formulas 1–4, wherein n=1 or m=1.

In all of formulas 1–4, preferred embodiments of $R^3$ are H and methyl, especially H.

$R^4$ is a fused or conjugated bicyclo aromatic system linked through a methylene group to the molecule. By "fused or conjugated bicyclo aromatic system" is meant a two-ringed system with aromatic character which may, further, contain one or more heteroatoms such as S, N, or O. When a heteroatom such as N is included, the system as it forms a part of formulas 1–4, may contain an acyl protecting group (1–5C) attached to the nitrogen. Representative bicyclo fused aromatic systems include naphthyl, indolyl, quinolinyl, and isoquinolinyl. Representative conjugated systems include biphenyl, 4-phenylpyrimidyl, 3-phenylpyridyl and the like. In all cases, any available position of the fused or conjugated bicyclic system can be used for attachment through the methylene. The fused or conjugated aromatic system may further be substituted by 1–2 alkyl (1–4C) residues and/or hydroxy or any ring nitrogens may be acylated. Preferred acylation is acetylation.

Preferred embodiments of $R^4$ include 1-(2-methyl naphthyl)methylene; 1-quinolyl methylene; 1-naphthyl methylene; 2-naphthyl methylene; 1-isoquinolyl methylene; 3-isoquinolyl methylene; 3-thionaphthenyl methylene; 3-cumaronyl methylene; 3-(5-methylindolyl)methylene; 3-(5-hydroxyindolyl)methylene; 3-(2-hydroxyindolyl)-methylene; biphenyl methylene; and 4-phenylpyrimidyl methylene; and the substituted forms thereof.

Many of these substituents as part of an amino acid residue are described in Greenstein and Winitz, "Chemistry of the Amino Acids" (1961) 3:2731–2741 (John Wiley & Sons, N.Y.).

A particularly preferred embodiment of $R^4$ is 3-indolylmethylene or its N-acylated derivative—i.e., that embodiment wherein the "C-terminal" amino acid is a tryptophan residue or a protected form thereof. A preferred configuration at the carbon to which $R^4$ is bound is that corresponding to L-tryptophan.

Preferred embodiments of X are those of the formula $NHR^5$ wherein $R^5$ is H, substituted or unsubstituted alkyl (1–12C) or aryl alkyl (6–12C). Particularly preferred substitutions on $R^5$ are a hydroxyl group, or a phenylmethoxycarbamyl (CBZ) residue. In addition, the compound may be extended by embodiments wherein X is an additional amino acid residue, particularly a glycyl residue, which may also be amidated as described.

In general, the compounds that are hydroxamates are obtained by converting a carboxylic acid or ester precursor of the formulas

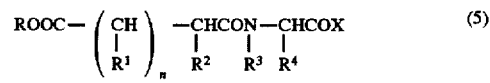

or

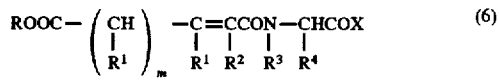

wherein R is H or alkyl (1–6C) to the corresponding hydroxamates by treating these compounds or their activated forms with hydroxylamine under conditions which effect the conversion.

With respect to starting materials, the components forming the $-NR^3-CHR^4COX$ moiety are readily available in the case of tryptophan and its analogs as esters or amides. As set forth above, many analogous fused bicyclo aromatic amino acids are described by Greenstein and Winitz (supra). Amino acids corresponding to those wherein $R^4$ is 1-(2-methyl naphthyl)methylene; 1-quinolyl-methylene; 1-naphthyl methylene; 1-isoquinolyl methylene; and 3-isoquinolyl methylene can be prepared from the bicyclo aromatic methylene halides using the acetamido malonic ester synthesis of amino acids, as is well understood in the art. The methylene halides themselves can be prepared from their corresponding carboxylic acids by reduction with lithium aluminum hydride and bromination of the resulting alcohol with thionyl bromide.

In general, the hydroxylamine reagent is formed in situ by mixing the hydroxylamine hydrochloride salt with an excess of KOH in methanol and removing the precipitated potassium chloride by filtration. The filtrate is then stirred with the precursor activated carboxylic acid or ester of formula 5 or 6 for several hours at room temperature, and the mixture is then evaporated to dryness under reduced pressure. The residue is acidified, then extracted with a suitable organic solvent such as ethyl acetate, the extract washed with aqueous potassium bisulfate and salt, and then dried with a solid drying agent such as anhydrous magnesium sulfate. The extract is then again evaporated to dryness and crystallized.

The substituted forms of the hydroxamate which include $-NHOR^7$ are synthesized in an analogous manner but substituting $H_2NOR^7$, wherein $R^7$ is lower alkyl or acyl (1–4C) for hydroxylamine per se. The resulting O-alkyl or acyl hydroxamate can then be further alkylated, if desired, to obtain the $R^7ONR^6$— derivative of the carboxylic acid. Similarly, $HNR^6OH$ may be reacted with the carboxylic acid to obtain the $HONR^6$— derivative. $HNCH_3OH$ and $H_2NOCH_3$ are commercially available.

To prepare the starting materials of formulae 5 and 6, the monoesterified carboxylic acid of the formula

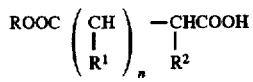

or of the formula

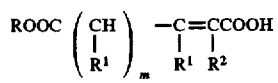

is reacted with the acid of the formula
$NHR^3CHR^4COX$
wherein X is other than OH under conditions wherein the condensation to form the amide bond occurs. Such conditions typically comprise mixture of the two components in a nonaqueous anhydrous polar aprotic solvent in the presence of a base and a condensing agent such as a carbodiimide. Thus, the formation of the amide linkage can be catalyzed in the presence of standard dehydration agents such as the carbodiimides, for example dicyclohexyl carbodiimide, or N, N-carbonyl diimidazole. The product is then recovered as a mixture of diastereomers of formula 5 or 6. This mixture is preferably used for the conversion to the hydroxamate and one of the resulting diastereomers is crystallized directly from the product mixture. Alternatively, the diastereomers are separated by flash chromatography before conversion to the hydroxamate and recovered separately. This process is less preferred as compared to the process wherein separation of the diastereomers is reserved until the final product is obtained.

In the notation used in the examples, the "A" isomer is defined as that which migrates faster on TLC; the "B" isomer as that which migrates more slowly. When the "L" form of tryptophan or an other amino acid containing a fused bicycloaromatic ring system is used as the residue, and $R^1$ is H, in general, the "A" form is that which contains the corresponding configuration at the carbon containing the $R^2$ substituent (providing that is the only other center of asymmetry) in the final hydroxamate product. However, in Example 2, below, where D-tryptophan is included in the composition, the "B" isomer contains what would correspond to an "L" configuration at the carbon containing $R^2$ in the compounds of formula 1.

When $R^6$ and/or $R^7$=alkyl, the corresponding O- or N-alkyl hydroxylamine is reacted with the methyl ester 4A as performed for unsubstituted hydroxylamine in Example 1. Alternatively, the methyl ester 4A can be saponified to its corresponding carboxylic acid and activated with oxalyl chloride or other condensing agent. The alkyl hydroxylamine can then be reacted with the activated carboxylic acid to give the O- or N-substituted hydroxamic acid. O- and N-methylhydroxylamine can be purchased from the Aldrich Chemical Company.

Other N-alkyl hydroxylamines can be synthesized by conversion of aliphatic aldehydes to their oximes, followed by reduction to the N-alkyl hydroxylamine with borane-pyridine complex in the presence of 6N HCl (Kawase, M. and Kikugawa, Y. J., *Chem Soc, Perkin Trans* (1979) 1:643. Other O-alkyl hydroxylamines can be synthesized by the general methods given by Roberts, J. S., "Derivatives of Hydroxylamine," Chapter 6.4 in Barton, D., et al., eds., *Comprehensive Organic Chemistry* (1979) 2:187–188 (Pergamon Press, Oxford). The two general methods employed are displacement by $R^7O^-$ of a leaving group from hydroxylamine sulfonic acid or chloramine, and O-alkylation of a hydroxamic acid with $R^7$—X followed by hydrolysis:

or

For $R^7$=acyl, a hydroxamic acid of this invention can be acylated with an acid chloride, anhydride, or other acylating agent to give the compounds of this class.

In some cases the derivatized maleic and succinic acid residues required for synthesis of the invention compounds are commercially available. If not, these can readily be prepared, in embodiments wherein $R^1$ is H or alkyl (1–8C) by reaction of a 2-oxocarboxylic ester of the formula $R^2COCOOR'$ in a Wittig reaction with an alkyl triphenylphosphoranylidene acetate or α-triphenylphosphoranylidene alkanoate. The methyl acetate or alkanoate is preferred, but any suitable ester can be employed. This reaction is conducted in a nonaqueous, nonpolar solvent usually at room temperature. The resultant compound is of the formula $ROOCCR^1=CR^2COOR'$, wherein R and R' are residues of esterifying alkyl or arylalkyl alcohols.

If the compounds of formula 6 are desired, this product is condensed with the appropriate tryptophan or analogous derivative; if the compounds of formula 5 are desired, the intermediate is reduced using hydrogen with a suitable catalyst. The sequence of reactions to obtain those embodiments wherein $R^1$ is H or alkyl, n is 1 and m is 0, and $R^2$ is alkyl are shown in Reaction Scheme 1.

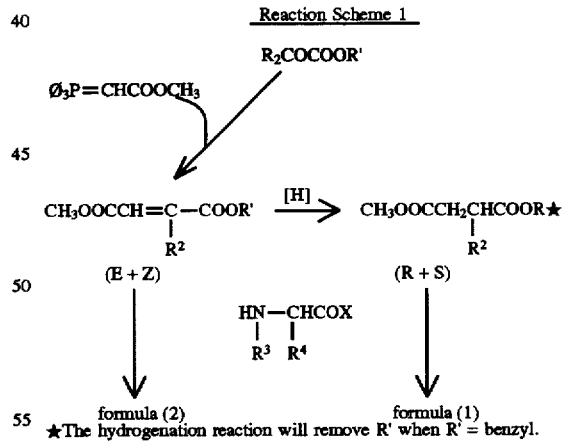

★The hydrogenation reaction will remove R' when R' = benzyl.

For those embodiments wherein $R^1$ and $R^2$ taken together are $(CH_2)_p$, the compounds of the invention are prepared analogously to the manner set forth in Reaction Scheme 1, except that the intermediate of the formula $ROOCCHR^1CHR^2COOH$ is prepared from the corresponding 1,2-cycloalkane dicarboxylic acid—i.e., 1,2-cyclopentane dicarboxylic acid anhydride; 1,2-cyclohexane dicarboxylic anhydride or 1,2-cycloheptane dicarboxylic anhydride.

For compounds wherein —$CONR^3$— is in modified isosteric form, these forms can be prepared by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J pept Prot Res* (1979) 14:177–185 (—$CH_2NR^3$—, —$CH_2CHR^3$—); Spatola, A. F., et al., *Life Sci* (1986) 38:1243–1249 (—$CH_2$—S); Hann, M. M., *J Chem Soc Perkin Trans 1* (1982) 307–314 (—CH=$CR^3$—, cis and trans); Almquist, R. G., et al., *J Med Chem* (1980) 23:1392–1398 (—$COCHR^3$—); Jennings-White, C., et al., *Tetrahedron Lett* (1982) 23:2533 (—$COCHR^3$—); Szelke, M., et al., European Application EP 45665 (1982) CA:97:39405 (1982) (—$CH(OH)CHR^3$—); Holladay, M. W., et al., *Tetrahedron Lett* (1983) 24:4401–4404 (—C(OH)$CH_2$—); and Hruby, V. J., *Life Sci* (1982) 31:189–199 (—$CH_2$—S—).

Preferred compounds of formula (1) or (2) include:
HONHCOCH$_2$CH(n-hexyl)-CO-L-Trp-NHMe;
HONHCOCH$_2$CH(n-pentyl)-CO-L-Trp-NHMe;
HONHCOCH$_2$CH(i-pentyl)-CO-L-Trp-NHMe;
HONHCOCH$_2$CH(ethyl)-CO-L-Trp-NHMe;
HONHCOCH$_2$CH(ethyl)-CO-L-Trp-NHCH$_2$CH$_3$;
HONHCOCH$_2$CH(ethyl)-CO-L-Trp-NHCH$_2$CH$_2$OH;
HONHCOCH$_2$CH(ethyl)-CO-L-Trp-NHcyclohexyl;
MeONHCOCH$_2$CH(iBu)-CO-L-Trp-NHEt;
EtONMeCOCH$_2$CH(iBu)-CO-L-Trp-NHEt;
MeONHCOCH$_2$CH(iBu)-CO-L-Ala(2-naphthyl)-NHEt;
EtONMeCOCH$_2$CH(iBu)-CO-L-Ala(2-naphthyl)-NHEt;
HONHCOCH$_2$CH(i-Bu)CO-L-Trp-NHMe;
HONHCOCH$_2$CH(i-Bu)CO-L-N-MeTrp-NHMe;
HONHCOCH$_2$CH(i-Bu)CO-L-Trp-NH(CH$_2$)$_2$OH;
HONHCOCH$_2$CH(i-Bu)CO-L-Trp-NH(S)CHMePh;
HONHCOCH$_2$CH(i-Bu)CO-L-Trp-NH(CH$_2$)$_6$NH-CBZ;
HONHCOCH$_2$CH(i-Bu)CO-L-Ala(2-naphthyl)NHMe;
HONHCOCH$_2$CH(i-Bu)CO-L-Trp-NH(CH$_2$)$_4$CH$_3$;
HONHCOCH$_2$CH(i-Bu)CO-L-Trp-piperidine;
HONHCOCH$_2$CH(i-Bu)CO-L-Trp-NH(CH$_2$)$_{11}$CH$_3$;
HONHCOCH$_2$CH(i-Bu)CO-L-Trp-NHcyclohexyl;
HONHCOCH$_2$CH(i-Bu)-L-Trp-OH;
HONMeCOCH$_2$CH(i-Bu)CO-L-Trp-NHMe;
HONEtCOCH$_2$CH(i-Bu)CO-L-Trp-NHMe;
CH$_3$COONHCOCH$_2$CH(i-Bu)CO-L-Trp-NHMe;
ΦCOONHCOCH$_2$CH(i-Bu)CO-L-Trp-NHMe;
CH$_3$COONMeCOCH$_2$CH(i-Bu)CO-L-Trp-NHMe; and
ΦCOONEtCOCH$_2$CH(i-Bu)CO-L-Trp-NHMe.

The reverse hydroxamates and hydroxyureas of formulae 3 and 4 are more stable biologically than the corresponding hydroxamates per se. This has been confirmed in Carter, G. W., et al., *J Pharmacol Exp Ther* (1991) 256:929–937; Jackson, W. P., et al., *J Med Chem* (1988) 31:499–500; Young, P. R., et al., *FASEB J* (1991) 5:A1273; Hahn, R. A., et al., *J Pharmacol Ex Ther* (1991) 256:94–102; Tramposch, K. M., et al., *Agents Actions* (1990) 30:443–450; Argentieri, D. C., et al.; Kimball, E., et al., *5th Int Conf Inflammation Research Assoc.*, Whitehaven, Pa., Sep. 23–27, 1990, Abstract 100; and Huang, F., et al., *J Med Chem* (1989) 32:1836–1842. Thus, while somewhat more complicated to synthesize, these analogs offer physiological characteristics which are advantageous in the applications of these compounds to therapy.

The reverse hydroxamates and hydroxyureas of the invention are obtainable using the standard techniques of synthetic organic chemistry (see Challis, B. C., et al., "Amides and Related Compounds" in "Comprehensive Organic Chemistry," Barton, D., et al., eds. (1979) 2:1036–1045), Pergamon Press, Oxford, as further described below.

With respect to starting materials, the components forming the —NR$^3$—CHR$^4$COX moiety are readily available in the case of tryptophan and its analogs as esters or amides. As set forth above, many analogous fused bicyclo aromatic amino acids are described by Greenstein and Winitz (supra). Amino acids corresponding to those wherein R$^4$ is 1-(2-methyl naphthyl)methylene; 1-quinolyl-methylene; 1-naphthyl methylene; 1-isoquinolyl methylene; and 3-isoquinolyl methylene can be prepared from the bicyclo aromatic methylene halides using the acetamido malonic ester synthesis of amino acids, as is well understood in the art. The methylene halides themselves can be prepared from their corresponding carboxylic acids by reduction with lithium aluminum hydride and bromination of the resulting alcohol with thionyl bromide.

Depending on the functional group symbolized by Y, the stage of synthesis at which this moiety is brought into the compound of the invention varies.

For those embodiments wherein Y is R$^7$ONR$^6$CONR$^6$— and wherein n=0, 1 or 2, the compounds are prepared by acylating an α, β or γ amino acid, respectively with methyl or ethyl chloroformate, condensing the resulting amino acid with a protected form of the moiety —NR$^3$CHR$^4$COX and reacting the resulting carboethoxy "dipeptide" with hydroxylamine or a substituted hydroxylamine as described by Fieser, L. F., et al., "Reagents for Organic Synthesis" (1967) 1:479 (John Wiley & Sons, New York). This sequence of reactions is shown in Reaction Scheme 1A.

REACTION SCHEME 1A

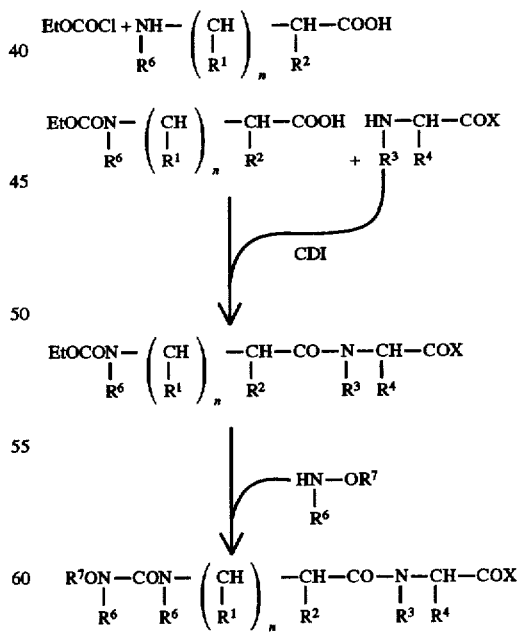

Alternatively, the α, β or γ amino acid is temporarily protected using, for example, carbobenzoxy or tertiary butyloxycarbonyl and coupling it to the carboxy-terminal-protected amino acid moiety containing R$^4$. The protecting group is then removed by hydrogenolysis or acidolysis as appropriate, and the deprotected α, β or γ amino group is reacted with an activated carbonic acid such as carbonyldiimidazole. The resultant is then reacted with hydroxylamine or substituted hydroxylamine to obtain the desired product. This sequence of reactions is summarized in Reaction Scheme 2. (In the formula Im-Co-Im, Im represents an imidazole residue.)

REACTION SCHEME 2

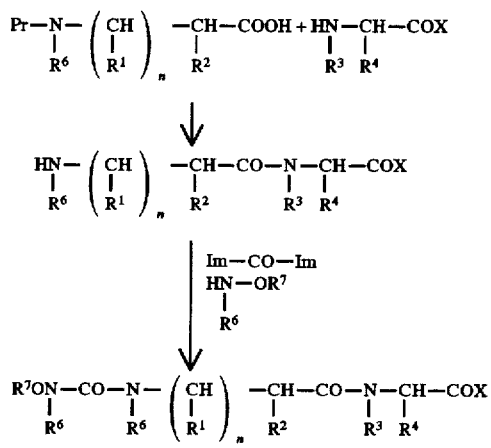

The appropriate α, β or γ amino acids are prepared by general methods as set forth by Jones, J. H., et al., in "Amino Acids," p. 834 (Barton, D., et al., eds.) ("Comprehensive Organic Chemistry" (1979) Vol. 2, Pergamon Press). Such methods include, for example, homologation by Arndt-Eistert synthesis of the corresponding N-protected α-amino acid and more generally the addition of nitrogen nucleophiles such as phthalimide to α,β-unsaturated esters, acids or nitriles.

In a second class of hydroxyureas, Y has the formula $R^6{}_2NCONOR^7$— and n is 0, 1 or 2. These compounds are prepared from the corresponding α,β or γ hydroxyamino acids of the formula $R^7ONH(CHR^1)_nCHR^2COOH$. When both $R^6$ are H, this intermediate is converted to the desired hydroxyurea by reaction with silicon tetraisocyanate, as described by Fieser and Fieser, "Reagents for Organic Synthesis" (1968) 1:479 (John Wiley & Sons, New York). The reaction is conducted with the hydroxyl group protected or substituted by $R^7$. The resulting hydroxyurea is then coupled to the component of the formula $HNR^3CHR^4COX$ to obtain the desired product. Alternatively, the amide is first formed and the N-hydroxyl dipeptide is treated with the reagent.

Alternatively, when Y is $R^6HNCO$—$NOR^7$, wherein $R^6$ is alkyl, the above O-protected α, β or γ N-hydroxyamino acid is reacted with the relevant alkylisocyanate $R^6NCO$ to produce the desired product.

When Y is of the formula $R^6{}_2NCO$—$NOR^7$— wherein both $R^6$ are alkyl, the α, β or γ N-hydroxyamino acid is reacted with an activated form of carbonic acid, for example, carbonyldiimidazole or bis-p-nitrophenylcarbonate, and then with the diamine $R^6{}_2$ NH wherein both $R^6$ are alkyl groups. This is followed by deprotection, if desired.

Conditions for the foregoing can be found in the descriptions of analogous preparations for tripeptides as described by Nishino, N., et al., *Biochemistry* (1979) 18:4340-4346.

The β-N-hydroxyamino acids used as intermediates in the foregoing synthesis can be prepared by a malonic ester synthesis in which diethyl malonate is alkylated twice, once with $R^2$—Br and then with benzylchloromethyl ether, for example, for the case wherein $R^1$ is H. The product is saponified, decarboxylated, hydrogenated, and oxidized to give the β-aldehyde in a manner similar to the synthesis of a homologous aldehyde described by Kortylewicz, Z. P., et al., *Biochemistry* (1984) 23:2083-2087. The desired β-hydroxyamino acid is then obtained by addition of protected (or alkylated, if $R^7$ is alkyl or acylated if R7 is acyl) hydroxylamine. The corresponding compound wherein $R^1$ is alkyl can be prepared in an analogous manner wherein the second alkylation utilizes benzyl-O—$CHR^1Cl$. The homologous ketone was described by Galardy, R. E., et al., *Biochemistry* (1985) 24:7607-7612.

Finally, those compounds wherein Y is of the formula $R^6CONOR^7$—, i.e., the reverse hydroxymates, can be prepared by acylation of the corresponding α, β or γ N-hydroxy dipeptide. Alternatively, the N-hydroxyamino acid can be acylated, followed by condensation to form the amide bond in the compounds of the invention. The acylation method is described by, for example, Nishino, N., et al., *Biochemistry* (1979) 18:4340-4346, cited above.

Alternatively, for those compounds wherein n=1 and $R^1$ is H, the compounds can be prepared by condensing the ylide 1,1-dimethoxy-2-(triphenylphosphoranylidene) ethane prepared from triphenylphosphine and 1,1-dimethoxy-2-bromoethane with 4-methyl-2-oxopentanoic acid. The product is then hydrogenated to obtain 4,4-dimethoxy-2-isobutylbutanoic acid which is coupled to the moiety $R^3NHCHR^4COX$ to obtain 4,4-dimethoxy-2-isobutylbutanoyl-$NR^3CHR^4COX$. Treatment with aqueous acid yields the aldehyde 2-isobutyl-4-oxobutanoyl-$NR^3CHR^4COX$. The oxime is prepared by reaction with hydroxylamine and reduced to the corresponding N-substituted hydroxylamine. Acylation of both the hydroxaminol oxygen and nitrogen followed by hydrolysis of the O-acyl group provides the N-acyl reverse hydroxymates. (Summers, J. B., et al., *J Med Chem* (1988) 31:1960-1964.)

For compounds wherein —$CONR^3$— is in modified isosteric form, these forms can be prepared by methods known in the art, as set forth above.

Preferred compounds of formulas (3) and (4) include:

EtONHCONMe-CH₂CH(iBu)-CO-L-Trp-NHEt;

EtCONOH-CH₂CH(iBu)-CO-L-Trp-NHEt;

n-PrCONOEt-CH₂CH(iBu)-CO-L-Trp-NHEt;

EtNHCONOMe-CH₂CH(iBu)-CO-L-Trp-NHEt;

MeNHCONOH-CH₂CH(iBu)-CO-L-Trp-NHEt;

EtONHCONMe-CH₂CH(iBu)-CO-L-Ala(2-naphthyl)-NHEt;

EtCONOH-CH₂CH(iBu)-CO-L-Ala(2-naphthyl)-NHEt;

n-PrCONOEt-CH₂CH(iBu)-CO-L-Ala(2-naphthyl)-NHEt;

EtNHCONOMe-CH₂CH(iBu)-CO-L-Ala(2-naphthyl)-NHEt;

MeNHCONOH-CH₂CH(iBu)-CO-L-Ala(2-naphthyl)-NHEt;

HONHCONHCH₂CH(iBu)-CO-L-TrpNHMe;

HONHCONHCH₂CH₂CH(iBu)-CO-L-TrpNHMe;

HONHCONHCH(iBu)CO-L-TrpNHMe;

H₂NCON(OH)CH(iBu)CO-L-TrpNHMe;

N(OH)CH₂CH(iBu)CO-L-TrpNHMe;

H₂NCON(OH)CH₂CH(iBu)CO-L-TrpNHMe;

CH₃CON(OH)CH(iBu)CO-L-TrpNHMe;

CH₃CON(OH)CH₂CH(iBu)CO-L-TrpNHMe; and

CH₃CON(OH)CH₂CH₂CH(iBu)CO-L-TrpNHMe.

ADMINISTRATION AND USE

As set forth in the Background section above, a number of diseases are known to be mediated by excess or undesired matrix-destroying metalloprotease activity. These include tumor metastasis, rheumatoid arthritis, skin inflammation, ulcerations, particularly of the cornea, reaction to infection, and the like. Thus, the compounds of the invention are useful in therapy with regard to conditions involving this unwanted activity.

Compounds which are synthetic inhibitors of mammalian metalloproteases are useful to inhibit angiogenesis. These compounds can therefore be formulated into pharmaceutical compositions for use in inhibiting angiogenesis in conditions characterized by an unwanted level of such blood vessel growth.

Standard pharmaceutical formulation techniques are used, such as those disclosed in *Remington's Pharmaceutical Sciences*, Mack Publishing Company, Easton, Pa., latest edition.

For indications to be treated systemically, it is preferred that the compounds be injected. These conditions include tumor growth and metastasis. The compounds can be formulated for injection using excipients conventional for such purpose such as physiological saline, Hank's solution, Ringer's solution, and the like. Injection can be intravenous, intramuscular, intraperitoneal or subcutaneous. Dosage levels are of the order of 0.1 µg/kg of subject to 1 mg/kg of subject, depending, of course, on the nature of the condition, the nature of the subject, the particular embodiment of the invention compounds chosen, and the nature of the formulation and route of administration.

In addition to administration by injection, the compounds of the invention can also be formulated into compositions for transdermal or transmucosal delivery by including agents which effect penetration of these tissues, such as bile salts, fusidic acid derivatives, cholic acid, and the like. The compounds can also be used in liposome-based delivery systems and in formulations for topical and oral administration depending on the nature of the condition to be treated. Oral administration is especially advantageous for those compounds wherein the moiety —CONR$^3$— is in a modified isosteric form. These compounds resist the hydrolytic action of the digestive tract. Oral formulations include syrups, tablets, capsules, and the like, or the compound may be administered in food or juice.

The inhibitors of the invention can be targeted to specific locations where vascularization is occurring by using targeting ligands. For example, to focus the compounds to a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the compounds to the targeting ligand are well known and are similar to a those described below for coupling to carrier. The conjugates are formulated and administered as described above.

For localized conditions, topical administration is preferred. For example, to treat diabetes-induced retinopathy or other neovascular glaucomas, direct application to the affected eye may employ a formulation such as eyedrops or aerosol. For this treatment, the compounds of the invention can also be formulated as gels or ointments, or can be incorporated into collagen or a hydrophilic polymer shield. The materials can also be inserted as a contact lens or reservoir or as a subconjunctival formulation.

Particular topical conditions that are susceptible to treatment using the compounds of the invention include stomach ulcers, superficial wounds of any type, epidermolysis bullosa, various forms of skin cancer, and pemphigus. It is well known that collagenase is involved in the progress of stomach ulcers, as described by Hasabe, T., et al., *J Exp Clin Med* (1987) 12:181–190; Ozaki, L, et al., *Scand J Gastroenterol Suppl (Norway)* (1989) 16:138–141. Collagenase is also found in marginal wound tissue as reviewed by Mullins, D. E., et al., *Biochim Biophys Acta* (1983) 695:177–214, and patients showing impaired wound healing are known to have increased collagenase activity in the wound tissue. For example, Hennesey, P. J., et al., *J Pediat Surg* (1990) 25:75–78, showed this to be the case in diabetes; Sank, A., et al., *Surgery* (1989) 106:1141–1148, demonstrated this enhanced collagenase activity in paraplegia, chronic renal failure, and Cushings disease. Thus, the collagenase inhibitors of the invention are useful in any ulcerative skin condition, including, for example, decubitus ulcers, or other conditions where wound healing is slow; other condition susceptible to treatment by the compounds of the invention include cornea or scleral melting associated with keratomalacia, scleromalacia perforans and connective tissue diseases.

This is also the case with respect to wounds inflicted in the course of medical treatment. It has been demonstrated that collagenase inhibitors enhance the strength of suture lines and suture holding capacity in intestinal anastomoses in rats (Hogstrom, H., et al., *Res Exp Med* (1985) 185:451–455. Other topical conditions responsive to the collagenase inhibitors of the invention include epidermolysis bullosa where increased collagenase activity has been demonstrated (Perez-Tamayo, R., *Am J Path* (1978) 92:509–566, pp. 539–541). It is also known that collagenase activity is increased in the stroma surrounding basal cell carcinoma and throughout tumor stromas in ulcerated basal cell carcinoma (Childer, S., J. W., et al., *J Am Acad Dermatol* (1987) 17:1025–1032).

Further, the matrix metalloprotease inhibitors of the invention are useful in the treatment of septic shock and in the treatment of adult respiratory distress syndrome (ARDS). The role of plasma proteases in septic shock has been shown by Colman, F. C., *New Eng J Med* (1989) 320:1207–1210, and the participation of neutrophil proteases in both septic shock and ARDS has been shown by Idell, S., et al., *Ann Res Respir Dis* (1985) 132:1098–1105. In the case of these conditions, the compounds of the invention protect the connective tissue directly from digestion by matrix metalloproteases as well as prevent the degradation of collagen and therefore prevent known chemotaxis of neutrophils toward collagen fragments (Werb, Z., in "Textbook of Rheumatology," Kelley, W. N., et al., eds. (1989) W. B. Saunders, Philadelphia, 3rd ed., pp. 300–320). The compounds of the invention also prevent the inactivation of plasma protease inhibitors by matrix metalloproteases (Werb, Z. supra).

In all of the foregoing, of course, the compounds of the invention can be administered alone or as mixtures, and the compositions may further include additional drugs or excipients as appropriate for the indication.

Conditions that benefit from angiogenesis inhibition thus include, generally, cancer, including angiosarcoma, Kaposi's sarcoma, glioblastoma multiforme, hemangio blastoma, including von Hippel-Lindan disease and hemangio pericytoma; eye conditions, such as diabetic retinopathy and neovascular glaucoma; immune system conditions, such as rheumatoid arthritis, angiolymphoid hyperplasia with eosinophilia; and skin conditions, such as cavernous hemangioma (including Kasabach-Merritt syndrome) and psoriasis.

The following examples are intended to illustrate but not to limit the invention. These examples describe the preparation of certain compounds of the invention and their activity in inhibiting mammalian metalloproteases.

In the examples below, TLC solvent systems are as follows: (A) ethyl acetate/methanol (95:5); (B) ethyl acetate/methanol (25:5); (C) ethyl acetate; (D) ethyl acetate/methanol (30:5); (E) ethyl acetate/hexane (1:1); (F) chloroform/methanol/acetic acid (30:6:2); (G) chloroform/methanol/acetic acid (85:10:1).

EXAMPLE 1

Preparation of N-[D,L-2-isobutyl-3-(N'-hydroxycarbonylamido)-propanoyl]-tryptophan methylamide A suspension of 5 g (0.033 mol) of the sodium salt of 4-methyl-2-oxopentanoic acid and 5.65 g (0.033 mol) of benzyl bromide in 10 ml of anhydrous dimethylformamide was stirred for 4 days at room temperature. After evaporation of the solvent under reduced pressure the residue was diluted to 100 ml with hexane and washed with water (3×20 ml) and saturated sodium chloride and dried over anhydrous magnesium sulfate. Evaporation of solvent gave 6.4 g (88% yield) of the benzyl ester of 4-methyl-2-oxopentanoic acid (1) as a colorless oil.

A mixture of 6.4 g (0.029 mol) of (1) and 9.7 g (0.029 mol) of methyl(triphenylphosphoranylidene)acetate in 100 mL of dry methylene chloride was stirred for 12 hr at room temperature and evaporated to dryness. The residue was extracted with hexane (3×50 mL). The hexane solution was washed with 10% sodium bicarbonate (2×30 mL), water and saturated sodium chloride and dried over anhydrous magnesium sulfate. Evaporation of the solvent gave 8.01 g (100% yield) of benzyl 2-isobutyl-3-(methoxycarbonyl)-propionate (2) as a mixture of E and Z isomers.

A mixture of 8.01 g (0.029 mol) of (2) and 1 g of 10% palladium on carbon in 50 mL of methanol was hydrogenated at room temperature under 4 atmospheres of hydrogen gas for 8 hr. After removal of the catalyst by filtration the filtrate was evaporated to dryness under reduced pressure to give 4.7 g (86% yield) of 2-iso-butyl-3-(methoxycarbonyl)-propionic acid (3) as a colorless oil.

To a mixture of 0.85 g (4.5 mmol) of (3) and 0.57 g (4.5 mmol) of oxalyl chloride in 10 mL of dry methylene chloride 0.1 mL of anhydrous dimethylformamide was added. After stirring for 1 hr at room temperature the solvent was evaporated under reduced pressure and the residue was diluted to 5 mL with anhydrous dimethylformamide and 1.06 g (4.1 mmol) of the hydrochloride salt of L-tryptophan methylamide (Kortylewicz and Galardy, *J Med chem* (1990) 33:263–273) was added followed by addition of 1.3 mL (9.3 mmol) of triethylamine at −10° C. This was stirred for 7 hr at room temperature and evaporated to dryness at room temperature under reduced pressure. The residue was diluted to 150 mL with ethyl acetate and washed with water (2×15 mL), 10% potassium bisulfate (5×20 mL), 10% sodium bicarbonate (2×20 mL), saturated sodium chloride and dried over anhydrous magnesium sulfate and then evaporated to give 1.6 g (83% yield) of N-[D,L-2-isobutyl-3-(methoxycarbonyl)-propanoyl]-L-tryptophan methylamide 4 as a mixture of diastereomers, 4A and 4B.

Isomers 4A and 4B were separated by flash chromatography (silica gel, ethyl acetate).

Isomer 4A: mp=134°–137° C. $R_f(C)=0.37$.
Isomer 4B: mp=156°–158° C. $R_f(C)=0.2$.

Alternatively, the mixture of 4A and 4B was converted directly to its hydroxamate as described below. In this case, 5A was crystallized from the mixture of 5A and 5B.

A warm mixture of 0.22 g (3.96 mmol) of potassium hydroxide in 1 mL of methanol was added to a warm mixture of 0.184 g (2.65 mmol) of the hydrochloride salt of hydroxylamine. After cooling in ice under an argon atmosphere the potassium chloride was filtered off and 0.5 g (1.32 mmol) of (4A) was added to the filtrate. The resulting mixture was stirred for 7 hr at room temperature and evaporated to dryness under reduced pressure. The residue was suspended in 100 mL of ethyl acetate and washed with 10 mL of 10% potassium bisulfate, saturated sodium chloride and dried over anhydrous magnesium sulfate and evaporated to dryness under reduced pressure. The residue was crystallized from ethyl acetate to give 0.28 g (56% yield) of pure 5A.

Isomer 4B was converted to its corresponding hydroxamic acid 5B (72% yield) as described for 4A.

Isomer 5A: mp=176°–182 C. Rf(D)=0.45.
Isomer 5B: mp=157°–162 C. Rf(D)=0.39.

For the case wherein the 4A/4B mixture is used, the 5A can be crystallized directly from the residue as described above.

In a similar manner to that set forth above, but substituting for 4-methyl-2-oxopentanoic acid, 2-oxopentanoic acid, 3-methyl-2-oxobutyric acid, 2-oxo-hexanoic acid, 5-methyl-2-oxohexanoic acid, or 2-decanoic acid, the corresponding compounds of formula 1 are prepared wherein $R^1$ is H and $R^2$ is an n-propyl, i-propyl, n-butyl, 2-methylbutyl, and n-octyl, respectively. In addition, following the procedures set forth hereinabove in Example 1, but omitting the step of hydrogenating the intermediate obtained by the Wittig reaction, the corresponding compounds of formula 2 wherein $R^1$ is H and $R^2$ is as set forth above are obtained.

To synthesize the compounds containing acylated forms of the indolyl residue, the intermediate ester of formula 3 or 4 is deesterified and acylated prior to conversion to the hydroxamate. For illustration, 4A is deesterified with sodium hydroxide in ethanol and then acidified to give N-(L-2-isobutyl-3-carboxypropanoyl)-L-tryptophan methylamide, which is treated with the anhydride of an alkyl (1–4C) carboxylic acid to obtain N-(L-2-isobutyl-3-carboxypropanoyl)-L-((N-acyl)indolyl)-tryptophan methylamide. This intermediate is then treated with oxalyl chloride followed by hydroxylamine at low temperature to give the corresponding hydroxamate.

EXAMPLE 2

Preparation of N-[2-isobutyl-3-(N'-hydroxycarbonylamido)-propanoyl]-D-tryptophan methylamide (7B)

The mixture of the two diastereoisomers of N-[2-isobutyl-3-(methoxycarbonyl)-propanoyl]-D-tryptophan methyl amide 6A,B was prepared as described for 4A,B in Example 1. The mixture was crystallized from ethyl acetate to give, after two recrystallizations, 0.26 g (49%) of the pure diastereomer 6B: mp 155°–157° C., $R_f(C)=0.32$. 6B was converted into its hydroxamic acid 7B by the method described in Example 1 in 50% yield (119 mg): mp 157°–159° C., $R_f(D)=0.39$.

EXAMPLE 3

Preparation of N-[2-isobutyl-3-(N'-hydroxycarbonyl-amido)-propanoyl]-N-methyl-L-tryptophan methylamide (9A)

The reaction of N-methyl-L-tryptophanmethylamide, prepared as described in Example 1 for L-tryptophan methylamide, with 3 performed as described for 4 gave crude N-[D,L-2-isobutyl-3-(methoxycarbonyl)-propanoyl]-N-methyl-L-tryptophan methylamide 8A,B which was crystallized from ethyl acetate to give 76 mg (19% yield) of 8A: mp 171°–174° C., $R_f(C)$=0.40.

8A was converted into 9A by the method described in Example 1 in 45% yield (34 mg): mp 180°–183° C., $R_f(D)$=0.54.

EXAMPLE 4

Preparation of N-[2-isobutyl-3-(N-hydroxycarbonyl amido)-propanoyl]-L-3-(2-naphthyl)-alanine methylamide (11A)

N-[D,L-isobutyl-3-(methoxycarbonyl)-propanoyl]-L-3-(2-naphthyl)-alanine 10A was prepared as described in Example 1 from L-3-(2-naphthyl)-alanine methylamide and 3. The crude product was chromatographed on 60 g of silica gel in ethyl acetate:hexane 1:1 to yield 12 mg (5% yield) of 10A: mp 151°–158° C., $R_f(C)$=0.69.

10A was converted into the hydroxamate 11A as in Example 1 in 30% yield (3 mg): mp 179°–181° C. $R_f(D)$= 0.17. MS-FAB (m/z) 400 (M$^+$ +H).

EXAMPLE 5

Preparation of N-[2-isobutyl-3-(N'-hydroxycarbonyl amido)-propanoyl]-L-tryptophan 2-hydroxyethylamide (13A)

The hydrochloride salt of L-tryptophan 2-hydroxyethylamide was prepared and coupled with 3 as described for the hydrochloride salt of L-tryptophan methylamide in Example 1 except that 3 was activated with 1,1'-carbonyldiimidazole for 20 minutes in methylene chloride at room temperature. The crude product was a mixture of 0.7 g (67% yield) of the diastereoisomers 12A,B: $R_f(C)$ 12A 0.38, $R_f(C)$ 12B 0.19.

12A crystallized from ethyl acetate in 35% yield (0.18 g): mp 161°–163° C., $R_f(C)$=0.38.

12A was converted into N-[2-isobutyl-3-(N'-hydroxycarbonylamido)-propanoyl]-L-tryptophan 2-hydroxyethylamide 13A as in Example 1 in 35% yield (62 mg): $R_f(D)$=0.17, mp 162°–163° C. MS-FAB (m/z) 419 (M$^+$ +H).

EXAMPLE 6

Preparation of N-[2-isobutyl-3-(N'-hydroxycarbonyl amido)-propanoyl]-L-tryptophan amylamide (15A)

The hydrochloride salt of L-tryptophan amylamide was prepared as described in Example 1 for L-tryptophan methylamide and was reacted with 3 that had been activated with 1,1'-carbonyldiimidazole for 20 minutes in dichloromethane at room temperature. The mixture of the two diastereomers of N-[D,L-2-isobutyl-3-(methoxycarbonyl)-propanoyl]-L-tryptophan amylamide 14A,B (90% yield) was converted to its corresponding hydroxamic acids as described for 4A. Slow evaporation of the ethylacetate solution gave 0.343 g (71%) of 15A,B: mp 160°–163° C. MS-FAB (m/z) 445 (M$^+$ +H).

EXAMPLE 7

Preparation of N-[2-isobutyl-3-(N'-hydroxycarbonyl amido)-propanoyl]-L-tryptophan piperidinamide (17A,B)

L-tryptophan piperidinamide was reacted with 3 as performed in Example 1 for L-tryptophan methylamide to give 1.14 g (89% yield) of N-[D,L-2-isobutyl-3-(methoxycarbonyl)-propanoyl]-L-tryptophan piperidinamide 16A,B as a foam; $R_f(C)$(16A) 0.74, (16B) 0.67.

16A,B was converted into crude 17A,B identically to 4A in Example 1 in 88% yield (570 mg): $R_f(D)$(17A) 0.41, (17B) 0.30. Crude 17A,B was chromatographed on 180 g of silica gel in 12% isopropanol in ethyl acetate to give 140 mg (25% yield) of 17A,B after crystallization from ethyl acetate: mp 169°–170° C. MS-FAB (m/z) 443 (M$^+$ +H).

EXAMPLE 8

Preparation of N-[2-isobutyl-3-(N'-hydroxycarbonyl amido)-propanoyl]-L-tryptophan dodecylamide (19A)

The reaction of L-tryptophan dodecylamide was prepared in a manner analogous to that described for L-tryptophan methylamide in Example 1. This ester was reacted with 3 as described in Example 1 to give crude N-[D,L-isobutyl-3-(methoxycarbonyl)-propanol]-L-tryptophan dodecylamide 18A,B in 93% yield as a mixture of isomers 19A and 19B. This mixture was chromatographed on 150 g of silica gel in ethyl acetate:hexane, 1:2, to yield 0.62 g of the mixture of the two isomers: $R_f(E)$ 19A 0.37, $R_f(E)$ 19B 0.29.

Crystallization by slow evaporation from ethyl acetate gave 0.38 g of 18A contaminated by approximately 10% of 18B by TLC and NMR analysis: mp 133°–135° C. 18A was converted to its corresponding hydroxamic acid as described in Example 1, except that the potassium salt of 19A crystallized from the alkaline reaction mixture in 81% yield (222 mg). The potassium salt of 19A (54 mg) was dissolved in 2 mL of boiling methanol, a few drops of water were added, and the solution was acidified to pH 6 with 0.1N hydrochloric acid and diluted with water to give 50 mg (100% yield) of 19A: mp 155°–159° C., $R_f(D)$=0.49. MS-FAB (m/z) 543 (M$^+$ +H).

EXAMPLE 9

Preparation of N-[2-isobutyl-3-(N'-hydroxycarbonylamido) propanoyl]-L-tryptophan (S)-methylbenzylamide (21A)

The reaction of L-tryptophan (S)-methylbenzylamide with 3 was performed as described in Example 1 to give, after crystallization from ethyl acetate, 330 mg (51% yield) of N-[2-isobutyl-3-(methoxycarbonyl)-propanoyl]-L-tryptophan (S)-methylbenzylamide 20A: mp 160°–162° C., $R_f(C)$=0.77.

20A was converted into hydroxamate 21A by the identical method used in Example 1 in 38% yield (76 mg): mp 165°–166° C., $R_f(D)$=0.73. MS-FAB (m/z) 479 (M$^+$ +H).

EXAMPLE 10

Preparation of N-[L-2-isobutyl-3-(N'-hydroxycarbonylamido)-propanoyl]-L-tryptophan (6-phenylmethoxycarbonylamino-hexyl-1)amide (27A)

To prepare 1-amino-6-phenylmethoxycarbonylamino-hexane (23), an equimolar mixture (0.01 mol) of 1,6- diaminohexane and benzaldehyde in 25 mL of methylene chloride was stirred for 5 hr in the presence of 1.5 g of anhydrous magnesium sulfate at room temperature. After removing the drying agent by filtration the filtrate was evaporated to dryness under reduced pressure to give 2 g (100% yield) of crude 1-amino-6-phenylamino-hexane 22 as a colorless oil; NMR(CDCl$_3$) 1.1–1.9(m, 10H, hexane CH$_2$-2,-3,-4,-5, NH$_2$); 2.6(m, 2H, CH$_2$-1); 3.51(m, 2H, hexane CH$_2$-6); 7.1–7.8 (m, 5H, aromatic); 8.16(s, 1H, imine CH). To a mixture of 2 g (0.01 mol) of 22 and 1.4 mL (0.01 mol) of triethylamine in 20 mL of methylene chloride. Then 1.78 g (0.01 mol) of benzylchloroformate was added dropwise at −5° C. The resulting mixture was stirred for 0.5 hr at 0° C. and for 2 hr at room temperature then diluted to 50 mL with methylene chloride and washed with water (20 ml), 2% sodium bicarbonate (20 ml), water and saturated sodium chloride and dried over anhydrous magnesium sulfate. After evaporation of solvent under reduced pressure the residue was dissolved in 5 mL of ethanol and 10 mL of 2N hydrochloric acid was added. The resulting mixture was stirred for 6 hr at room temperature then evaporated to dryness under reduced pressure. The residue was diluted to 50 mL with water and washed with ethyl ether (2×15 ml). The water phase was evaporated under reduced pressure and the product 23 was purified by crystallization from a small portion of water with a yield of 42%; mp 175°–178° C.

To prepare the dipeptide analog (N-(L-2-isobutyl-3-methoxycarbonyl)-propanoyl-L-tryptophan (25A)), for derivatization to 23: To a mixture of 1.754 g (9.32 mmol) of 2-isobutyl-3-methoxycarbonylpropionic acid 3 in 4 mL of 50% anhydrous DMF in methylene chloride 1.66 g (10.2 mmol) of N,N'-carbonyldiimidazole (CDI) was added at room temperature. After 15 minutes of stirring at room temperature, 3.08 g (9.31 mmol) of the hydrochloride salt of L-tryptophan benzyl ester was added. The resulting mixture was stirred overnight at room temperature, then diluted to 60 mL with ethyl acetate and washed with 5% sodium bicarbonate (2×15 ml), water (2×15 ml), saturated sodium chloride solution and dried over magnesium sulfate. Evaporation of the solvent under reduced pressure gave 4.32 g (100% yield) of 24, the benzyl ester of 25 as a colorless foam, which was used in the next step without further purification.

Hydrogen gas was bubbled through a mixture of 4.32 g (9.31 mmol) of 24 and 0.5 g of 10% palladium on carbon in 15 mL of methanol for 2 hr while methanol was added to keep the volume of the reaction mixture constant. The catalyst was filtered off and washed with a fresh portion of methanol (15 ml) and the filtrate was evaporated to dryness under reduced pressure. Evaporation of the solvent under reduced pressure and drying of the residue in vacuo gave 3.08 g (88% yield) of acid 25A,B as a mixture of two diastereoisomers, in the form of a colorless glassy solid. This was separated to give isomers 25A and 25B by flash chromatography (silica gel; ethyl acetate; R$_f$(25A)=0.24, R$_f$(25B)=0.1).

The compound 25A was converted to N-[L-2-isobutyl-3-methoxycarbonylpropanoyl]-L-tryptophan (6-phenylmethoxycarbonylamino-hexyl-1)amide (26A) as follows. A mixture of 0.55 g (1.47 mmol) of 25A and 0.24 g (1.48 mmol) of CDI in 1 mL of 2% dimethylformamide in methylene chloride was stirred for 0.5 hr at room temperature and 0.42 g (1.47 mmol) of 23 was added. After stirring overnight at room temperature, the mixture was diluted to 50 mL with chloroform and washed with 2% potassium bisulfate (2×10 ml), water (10 ml), 5% sodium bicarbonate (2×10 ml), water (2×10 ml) and saturated sodium chloride and dried over anhydrous magnesium sulfate. Evaporation of the solvent under reduced pressure gave 0.8 g of the crude 26A which was purified by flash chromatography (silica gel; ethyl acetate/hexane 25:5): Yield 56%; R$_f$(E)=0.57.

When the product 26A is substituted for 4A in Example 1, the identical process afforded the title compound 27A, melting at 102°–108° C., in 46% yield; R$_f$(D)=0.63.

EXAMPLE 11

Preparation of N-[L-2-isobutyl-3-(N'-hydroxycarbonyl-amido)-propanoyl]-L-tryptophan cyclohexylamide (28A)

When cyclohexylamine is substituted for 23 in Example 10, the identical process afforded the title compound 28A melting at 199°–203° C., in 49% yield; R$_f$(D)=0.51.

EXAMPLE 12

Preparation of N-[cis-2-(N'-hydroxycarbonyl-amido)-cyclohexylcarbonyl]-L-tryptophan methylamide (29A,B)

A mixture of 2 g (0.013 mol) of cis-1,2-cyclohexanedicarboxylic anhydride in 15 mL of methanol was refluxed for 5 hr, then evaporated to dryness under reduced pressure to give 2.41 g (100% yield) of cis-2-methoxycarbonyl-cyclohexanecarboxylic acid. When this was substituted for 3 in Example 1, the identical process afforded the title compound, melting at 140°–144° C., in 36% yield; R$_f$(D)= 0.53, 0.47.

EXAMPLE 13

Preparation of N-[trans-2-(N'-hydroxycarbonyl-amido)-cyclohexylcarbonyl]-L-tryptophan methylamide (30A,B)

When (±)trans-1,2-cyclohexanedicarboxylic anhydride was substituted for cis-1,2-cyclohexanedicarboxylic anhydride in Example 12, the identical process afforded the title compound 30A,B, melting at 167°–174° C., in 37% yield; R$_f$(D)=0.57.

EXAMPLE 14

Preparation of N-[2-isobutyl-3-(N'-hydroxycarbonyl-amido)-propanoyl]-L-tryptophan (31A)

31A was prepared from 25A in Example 10 in a similar manner to the preparation of 5A in Example 1 in 75% yield (128 mg) and isolated as a foam from ethyl acetate: R$_f$(F) =0.55, MS-FAB (m/z) (M$^+$ +H). A small sample of 31A recrystallized from ethyl acetate had a melting point of 116°–120° C.

EXAMPLE 15

Preparation of N-(D,L-2-isobutyl-3-carboxypropanoyl)-L-tryptophan (6-aminohexyl-1) amide (32A)

A mixture of 0.5 g (8.24 mmol) of 26A in 0.4 mL of 2N potassium hydroxide in methanol was stirred overnight at room temperature, then evaporated to dryness under reduced pressure. The residue was diluted to 15 mL with water and acidified to pH=2 with 1N hydrochloric acid. The crude free acid of 26A was taken up with ethyl acetate (3×15 ml) and the organic phase was dried over anhydrous magnesium sulfate and evaporated to dryness to give 0.45 g (92% yield) of 26A as a colorless foam.

Hydrogen gas was bubbled through a mixture of 0.395 g (6.6 mmol) of the free acid of 26A in 15 mL of methanol for 2 hr, in the presence of 0.12 g of 10% palladium on carbon at room temperature. The catalyst was filtered off, washed with ethanol (2×20 ml) and the filtrate was evaporated to dryness under reduced pressure to give 0.3 g (92% yield) of the title compound 32A as a colorless foam; $R_f(G) = 0.08$.

EXAMPLE 16

Preparation of N-[N-(2-isobutyl-3-carboxypropanoyl)-L-tryptophanyl] glycine 34A,B The reaction of L-tryptophanyl-glycine methyl ester with acid 3, performed as described for 25A gave crude N-[N-(D,L-2-isobutyl-3-methoxycarbonylpropanoyl)-L-tryptophanyl]-glycine methyl ester 33 in 87% yield as a mixture of diastereomers 33A and 33B. Isomers 33A and 33B were separated by flash chromatography (silica gel; ethyl acetate). Isomer 33A mp=154°–155° C.; $R_f(C)=0.46$.

Esters 33A,B were transformed to free acids 34A,B by saponification with two equivalent of methanolic potassium hydroxide, as described for 25A. Isomer 34A yield 92%; mp=96°–102° C.; $R_f(G)=0.31$.

Isomer 34B yield 93%; mp=99°–105° C.; $R_f(G)=0.25$.

EXAMPLE 17

Preparation of N-(cis-2-carboxy-cyclohexylcarbonyl)-L-tryptophan methylamide 35

To a mixture of 0.281 g (1.82 mmol) of cis-1,2-cyclohexanedicarboxylic anhydride and 0.47 g of the hydrochloride salt of L-Trp-NHMe in 0.5 mL of dimethylformamide 0.51 mL of triethylamine was added at room temperature. After 2 hr of stirring the resulting mixture was diluted to 10 mL with water and 25 mL of ethyl acetate was added. The resulting mixture was acidified to pH=2 with 10% potassium bisulfate and the organic phase was washed with water (2×15 ml), saturated sodium chloride and dried over anhydrous magnesium sulfate and evaporated to dryness. The title compound 35 was purified by crystallization from an ethyl acetate-hexane mixture. Yield 48%; mp=105°–112° C.; $R_f(G)=0.65, 0.61$.

EXAMPLE 18

Preparation of N-(trans-2-carboxy-cyclohexylcarbonyl)-L-tryptophan methylamide 36

When (±) trans-1,2-cyclohexanedicarboxylic anhydride is substituted for cis-1,2-cyclohexane-dicarboxylic anhydride in Example 17, the identical process afforded the title compound 36 in 56% yield: mp=167°–174° C.; Rf(G)=0.67, 0.61.

EXAMPLE 19

Preparation of N-[2-isobutyl-3-(N'-acetoxycarbonylamido)-propanoyl]-L-tryptophan methylamide (37A)

To 97.5 mg (0.25 mmol) of 5A (Example 1) in 0.5 ml of dimethylformamide was added 25.5 mg (0.25 mmol) of acetic anhydride and 37 mg (0.25 mmol) of 1,8-diazabicyclo [5.4.0] undec-7-ene (DBU) at room temperature. After standing overnight, the DMF was evaporated under high vacuum and the residue taken up in a mixture of equal volumes of ethyl acetate and 2% potassium bisulfate. The ethyl acetate layer was washed with 2% potassium bisulfate, water, and brine, dried over magnesium sulfate, and evaporated to give a solid. The solid was dissolved in a 1:1 mixture of hot ethyl acetate:hexane, which upon standing at room temperature gave 71 mg (66% yield) of solid product 37A: mp=184°–186° C.; Rf(G)=0.68.

EXAMPLE 20

Preparation of N-[isobutyl-3-(N'-benzoxycarbonylamido)-propanoyl]-L-tryptophan methylamide (38A)

To 30.5 mg (0.25 mmol) of benzoic acid in 1 ml of tetrahydrofuran was added 40.5 mg (0.25 mmol) of carbonyldiimidazole. After 10 minutes, 97 mg (0.25 mmol) of compound 5A from Example 1 was added in 1 ml of dimethylformamide. After 10 minutes, the reaction mixture was evaporated to dryness under high vacuum, and dissolved in a mixture of equal volumes of ethyl acetate and water. The ethyl acetate layer was washed with 5% sodium bicarbonate, water, 2% sodium bisulfate, water, and brine, and dried over magnesium sulfate. Evaporation of the ethyl acetate layer to a small volume gave 50 mg (41%) of the title compound, 38A: mp=187°–187.5° C.; Fr(G)=0.54.

EXAMPLE 21

Applying the methods set forth above, the following invention compounds are synthesized:

HONHCOCH$_2$CH(n-hexyl)-CO-L-Trp-NHMe;
HONHCOCH$_2$CH(n-pentyl)-CO-L-Trp-NHMe;
HONHCOCH$_2$CH(i-pentyl)-CO-L-Trp-NHMe;
HONHCOCH$_2$CH(ethyl)-CO-L-Trp-NHMe;
HONHCOCH$_2$CH(ethyl)-CO-L-Trp-NHCH$_2$CH$_3$;
HONHCOCH$_2$CH(ethyl)-CO-L-Trp-NHCH$_2$CH$_2$OH;
HONHCOCH$_2$CH(ethyl)-CO-L-Trp-NHcyclohexyl;
MeONHCOCH$_2$CH(iBu)-CO-L-Trp-NHEt;
EtONMeCOCH$_2$CH(iBu)-CO-L-Trp-NHEt;
MeONHCOCH$_2$CH(iBu)-CO-L-Ala(2-naphthyl)-NHEt;
EtONMeCOCH$_2$CH(iBu)-CO-L-Ala(2-naphthyl)-NHEt;
EtONHCONMe-CH$_2$CH(iBu)-CO-L-Trp-NHEt;
EtCONOH-CH$_2$CH(iBu)-CO-L-Trp-NHEt;
n-PrCONOEt-CH$_2$CH(iBu)-CO-L-Trp-NHEt;
EtNHCONOMe-CH$_2$CH(iBu)-CO-L-Trp-NHEt;
MeNHCONOH-CH$_2$CH(iBu)-CO-L-Trp-NHEt;
EtONHCONMe-CH$_2$CH(iBu)-CO-L-Ala(2-naphthyl)-NHEt;
EtCONOH-CH$_2$CH(iBu)-CO-L-Ala(2-naphthyl)-NHEt;
n-PrCONOEt-CH$_2$CH(iBu)-CO-L-Ala(2-naphthyl)-NHEt;
EtNHCONOMe-CH$_2$CH(iBu)-CO-L-Ala(2-naphthyl)-NHEt;
MeNHCONOH-CH$_2$CH(iBu)-CO-L-Ala(2-naphthyl)-NHEt;
HONHCONHCH$_2$CH(iBu)-CO-L-TrpNHMe;
HONHCONHCH$_2$CH$_2$CH(iBu)-CO-L-TrpNHMe;
HONHCONHCH(iBu)CO-L-TrpNHMe;
H$_2$NCON(OH)CH(iBu)CO-L-TrpNHMe;
N(OH)CH$_2$CH(iBu)CO-L-TrpNHMe;
H$_2$NCON(OH)CH$_2$CH$_2$CH(iBu)CO-L-TrPNHMe;
CH$_3$CON(OH)CH(iBu)CO-L-TrpNHMe;

CH₃CON(OH)CH₂CH(iBu)CO-L-TrpNKMe; and
CH₃CON(OH)CH₂CH₂CH(iBu)CO-L-TrPNHMe.

Determination of the inhibitory activity of certain of the compounds prepared is conducted as described above, and provides the results shown in Table 1.

TABLE 1

| No. | | Compound | $K_i$ (nM) |
|---|---|---|---|
| 1 | 5A | NHOHCOCH₂CH(i-Bu)CO-L-Trp — NHMe | 10 |
| 1 | 5B | NHOHCOCH₂CH(i-Bu)CO-L-Trp — NHMe | 150 |
| 2 | 7A | NHOHCOCH₂CH(i-Bu)CO-D-Trp — NHMe | 70,000 |
| 3 | 9A | NHOHCOCH₂CH(i-Bu)CO-L-N — MeTrp — NHMe | 500 |
| 4 | 11A | NHOHCOCH₂CH(i-Bu)CO-L-Ala(2-naphthyl)NHMe | 15 |
| 5 | 13A | NHOHCOCH₂CH(i-Bu)CO-L-Trp — NH(CH₂)₂OH | 20 |
| 6 | 15A | NHOHCOCH₂CH(i-Bu)CO-L-Trp — NH(CH₂)₄CH₃ | 30 |
| 7 | 17A, B | NHOHCOCH₂CH(i-Bu)CO-L-Trp-piperidine | 200 |
| 8 | 19A | NHOHCOCH₂CH(i-Bu)CO-L-Trp — NH(CH₂)₁₁CH₃ | 300 |
| 9 | 21A | NHOHCOCH₂CH(i-Bu)CO-L-Trp — NH(S)CHMePh | 3 |
| 10 | 27A | NHOHCOCH₂CH(i-Bu)CO-L-Trp — NH(CH₂)₆NH — CBZ | 13 |
| 11 | 28A | NHOHCOCH₂CH(i-Bu)CO-L-Trp — NHcyclohexyl | 50 |
| 12 | 29A, B | cis-NHOHCO—(cyclohexyl)—CO—L-Trp—NHMe | >10,000 |
| 13 | 30A, B | trans-NHOHCO—(cyclohexyl)—CO—L-Trp—NHMe | >10,000 |
| 14 | 31A | NHOHCO — CH₂CH(i-Bu)-L-Trp — OH | 200 |
| 15 | 32A | HOOC — CH₂CH(i-Bu)CO-L-Trp — NH(CH₂)NH₂ | >10,000 |
| 16 | 34A | HOCO — CH₂CH(i-Bu)CO-L-Trp — Gly — OH | >10,000 |
|  | 34B | HOCO — CH₂CH(i-Bu)CO-L-Trp — Gly — OH | >10,000 |
| 17 | 35 | cis-HOCO—(cyclohexyl)—CO—L-Trp—NHMe | >10,000 |
| 18 | 36 | trans-HOCO—(cyclohexyl)—CO—L-Trp—NHMe | >10,000 |

EXAMPLE 22

Inhibition of Angiogenesis

A crude extract (30 mg/mL protein) of Walker 256 carcinoma, a rat malignant tumor, was incorporated into Hydron, a slow release polymer, in 1.5 mm diameter pellets. Pellets were implanted in the stroma of the corneas of anesthetized albino rats. A cannula was chronically implanted in the inferior vena cava, through which 10 mg/mL of compound 5A in 55% DMSO in water was infused continuously for six days at the rate of 0.8 mL/24 hr. Controls received only the DMSO solution. After six days, the animals were re-anesthetized and perfused intra-arterially with India ink in order to visualize the corneal vessels. The eyes were then enucleated and fixed in 5% formalin. Control eyes which received only the DMSO solution show massive vessel growth toward the pellet from the limbus. The animals receiving compound 5A show vessels much shorter and/or much finer than in the controls, barely filling with ink.

I claim:

1. A method for treating septic shock which method comprises administering to a patient an effective amount of a synthetic mammalian matrix metalloprotease inhibitor, wherein said inhibitor is of the formula:

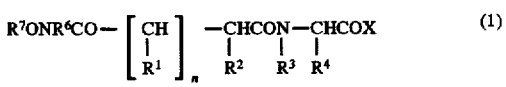

(1)

or

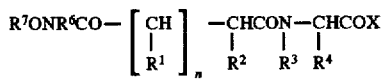

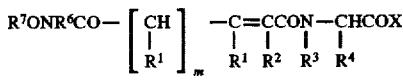

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl 6–16C); or X is an amino acid group or amide thereof; or X is a cyclic amine or heterocyclic amine; and $R^6$ is H or lower alkyl (1–4C); and $R^7$ is H, lower alkyl (1–4C) or an acyl group;

and wherein optionally substituted groups are substituted with non-interfering substituents.

4. A method for treating adult respiratory distress syndrome which method comprises administering to a patient an effective amount of a synthetic mammalian matrix metalloprotease inhibitor, wherein said inhibitor is of the formula:

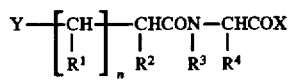

or

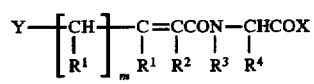

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine;

Y is selected from the group consisting of $R^7ONR^6CONR^6$—, $R^6{}_2NCONOR^7$, and $R^6CONOR^7$—, wherein each $R^6$ is independently H or lower alkyl (1–4C); $R^7$ is lower alkyl (1–4C) or an acyl group;

and wherein optionally substituted groups are substituted with non-interfering substituents.

5. A method for treating rheumatoid arthritis which method comprises administering to a patient an effective amount of a synthetic mammalian matrix metalloprotease

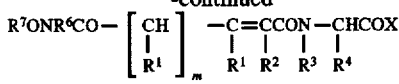

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine; and $R^6$ is H or lower alkyl (1–4C); and $R^7$ is H, lower alkyl (1–4C) or an acyl group;

and wherein optionally substituted groups are substituted with non-interfering substituents.

2. A method for treating septic shock which method comprises administering to a patient an effective amount of a synthetic mammalian matrix metalloprotease inhibitor, wherein said inhibitor is of the formula:

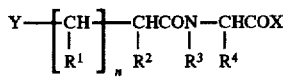

or

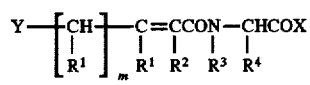

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine;

Y is selected from the group consisting of $R^7ONR^6CONR^6$—, $R^6{}_2NCONOR^7$, and $R^6CONOR^7$—, wherein each $R^6$ is independently H or lower alkyl (1–4C); $R^7$ is lower alkyl (1–4C) or an acyl group;

and wherein optionally substituted groups are substituted with non-interfering substituents.

3. A method for treating adult respiratory distress syndrome which method comprises administering to a patient an effective amount of a synthetic mammalian matrix metalloprotease inhibitor, wherein said inhibitor is of the formula:

inhibitor, wherein said inhibitor is of the formula:

 (1)

or

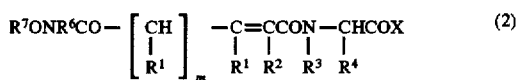 (2)

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine; and $R^6$ is H or lower alkyl (1–4C); and $R^7$ is H, lower alkyl (1–4C) or an acyl group;

and wherein optionally substituted groups are substituted with non-interfering substituents.

6. A method for treating rheumatoid arthritis which method comprises administering to a patient an effective amount of a synthetic mammalian matrix metalloprotease inhibitor, wherein said inhibitor is of the formula:

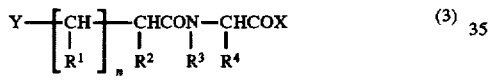 (3)

or

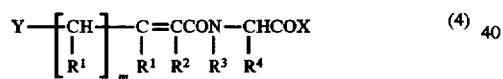 (4)

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–4C); or X is an amino acid group or amide thereof; or X is a cyclic amine or heterocyclic amine;

Y is selected from the group consisting of $R^7ONR^6CONR^6$—, $R^6{}_2NCONOR^7$, and $R^6CONOR^7$—, wherein each $R^6$ is independently H or lower alkyl (1–4C); $R^7$ is lower alkyl (1–4C) or an acyl group;

and wherein optionally substituted groups are substituted with non-interfering substituents.

7. A method for treating metastasis of tumor cells which method comprises administering to a patient an effective amount of a synthetic mammalian matrix metalloprotease inhibitor, wherein said inhibitor is of the formula:

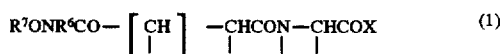 (1)

or

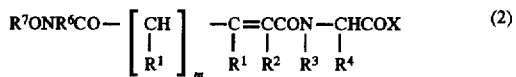 (2)

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine; and $R^6$ is H or lower alkyl (1–4C); and $R^7$ is H, lower alkyl (1–4C) or an acyl group;

and wherein optionally substituted groups are substituted with non-interfering substituents.

8. A method for treating metastasis of tumor cells which method comprises administering to a patient an effective amount of a synthetic mammalian matrix metalloprotease inhibitor, wherein said inhibitor is of the formula:

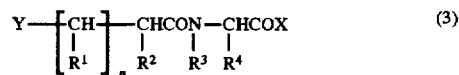 (3)

or

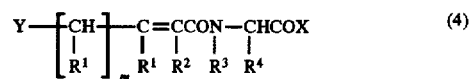 (4)

wherein each $R^1$ is independently H or alkyl (1–8C) and $R^2$ is alkyl 1–8C or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine;

Y is selected from the group consisting of $R^7ONR^6CONR^6$—, $R^6{}_2NCONOR^7$, and $R^6CONOR^7$—, wherein each $R^6$ is independently H or lower alkyl (1–4C); $R^7$ is lower alkyl (1–4C) or an acyl group;

and wherein optionally substituted groups are substituted with non-interfering substituents.

9. A method to inhibit anglogenesis which method comprises contacting a tissue in which unwanted anglogenesis is occurring with an effective amount of a synthetic mammalian matrix metalloprotease inhibitor, wherein said inhibitor is of the formula:

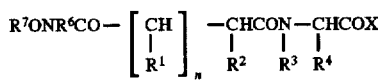

(1)

or

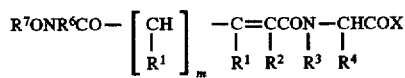

(2)

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl is (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine; and $R^6$ is H or lower alkyl (1–4C); and $R^7$ is H, lower alkyl (1–4C) or an acyl group;

and wherein optionally substituted groups are substituted with non-interfering substituents.

10. A method to inhibit angiogenesis which method comprises contacting a tissue in which unwanted angiogenesis is occurring with an effective amount of a synthetic mammalian matrix metalloprotease inhibitor, wherein said inhibitor is of the formula:

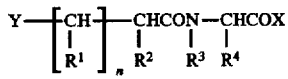

(3)

or

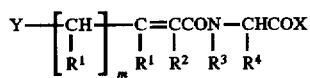

(4)

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine;

Y is selected from the group consisting of $R^7ONR^6CONR^6$—, $R^6{}_2NCONOR^7$, and $R^6CONOR^7$—, wherein each $R^6$ is independently H or lower alkyl (1–4C); $R^7$ is lower alkyl (1–4C) or an acyl group;

and wherein optionally substituted groups are substituted with non-interfering substituents.

11. A method for treating a malignant tumor which method comprises administering to a patient an effective amount of a synthetic mammalian matrix metalloprotease inhibitor, wherein said inhibitor is of the formula:

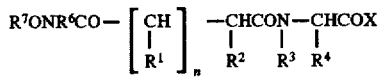

(1)

or

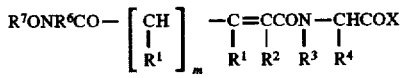

(2)

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine; and $R^6$ is H or lower alkyl (1–4C); and $R^7$ is H, lower alkyl (1–4C) or an acyl group;

and wherein optionally substituted groups are substituted with non-interfering substituents.

12. A method for treating a malignant tumor which method comprises administering to a patient an effective amount of a synthetic mammalian matrix metalloprotease inhibitor, wherein said inhibitor is of the formula:

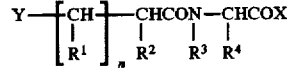

(3)

or

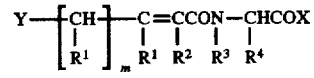

(4)

wherein each $R^1$ is independently H or alkyl (1–8C) and $R^2$ is alkyl (1–8C) or wherein the proximal $R^1$ and $R^2$ taken together are —$(CH_2)_p$— wherein p=3–5;

$R^3$ is H or alkyl (1–4C);

$R^4$ is fused or conjugated optionally substituted bicycloaryl methylene;

n is 0, 1 or 2;

m is 0 or 1; and

X is $OR^5$ or $NHR^5$, wherein $R^5$ is H or optionally substituted alkyl (1–12C), optionally substituted aryl (6–12C), optionally substituted aryl alkyl (6–16C); or X is an amino acid group or amide thereof; or X is a cyclic amine or heterocyclic amine;

Y is selected from the group consisting of $R^7ONR^6CONR^6$—, $R^6{}_2NCONOR^7$, and $R^6CONOR^7$—, wherein each $R^6$ is independently H or lower alkyl (1–4C); $R^7$ is H, lower alkyl (1–4C) or an acyl group;

and wherein optionally substituted groups are substituted with non-interfering substituents.

13. A method for treating a malignant tumor which method comprises administering to a patient an effective amount of a synthetic mammalian matrix metalloprotease inhibitor, wherein said inhibitor is of the formula: $NHOHCOCH_2CH(i\text{-}Bu)Co\text{-}L\text{-}Trp\text{-}NHMe$.

* * * * *